United States Patent
Okumura et al.

(10) Patent No.: US 9,964,491 B2
(45) Date of Patent: May 8, 2018

(54) METHOD AND DETECTION SYSTEM FOR DETECTING AN ANALYTE

(71) Applicant: PANASONIC CORPORATION, Osaka (JP)

(72) Inventors: Yasuaki Okumura, Kyoto (JP); Tatsurou Kawamura, Kyoto (JP); Masahiko Shioi, Kyoto (JP); Masaru Minamiguchi, Kyoto (JP)

(73) Assignee: PANASONIC CORPORATION, Osaka (JP)

( * ) Notice: Subject to any disclaimer, the term of this patent is extended or adjusted under 35 U.S.C. 154(b) by 449 days.

(21) Appl. No.: 14/705,343

(22) Filed: May 6, 2015

(65) Prior Publication Data

US 2015/0233836 A1 Aug. 20, 2015

Related U.S. Application Data

(63) Continuation of application No. PCT/JP2013/007312, filed on Dec. 12, 2013.

(30) Foreign Application Priority Data

Dec. 27, 2012 (JP) .................................. 2012-284183

(51) Int. Cl.
  *G01N 21/65* (2006.01)
  *A61B 5/00* (2006.01)
  (Continued)

(52) U.S. Cl.
  CPC ......... *G01N 21/658* (2013.01); *A61B 5/1455* (2013.01); *A61B 5/1459* (2013.01);
  (Continued)

(58) Field of Classification Search
  CPC ... A61B 5/145; A61B 5/1455; A61B 5/14503; A61B 5/14507; A61B 5/14532;
  (Continued)

(56) References Cited

U.S. PATENT DOCUMENTS

| 7,738,096 B2 * | 6/2010 | Zhao ........................ B82Y 5/00 356/301 |
| 2002/0072657 A1 * | 6/2002 | Bousquet ........... A61B 5/14532 600/310 |

(Continued)

FOREIGN PATENT DOCUMENTS

| JP | 2006-520216 A | 9/2006 |
| JP | 2008-528237 A | 7/2008 |

(Continued)

OTHER PUBLICATIONS

International Search Report issued in PCT/JP2013/007312, dated Feb. 18, 2014, with English translation.

*Primary Examiner* — Eric Winakur
*Assistant Examiner* — Chu Chuan (JJ) Liu
(74) *Attorney, Agent, or Firm* — McDermott Will & Emery LLP

(57) ABSTRACT

An exemplary sensor chip includes a substrate, a metal pattern formed on a side of the substrate that is irradiated with excitation light, and a first substance and a second substance provided near the metal pattern. A first intensity Xa of the first surface-enhanced Raman-scattered light from the first substance and a second intensity Xb of the second surface-enhanced Raman-scattered light from the second substance are detected. An intensity ratio Xc, as obtained by dividing the second intensity Xb with the first intensity Xa, is calculated.

12 Claims, 6 Drawing Sheets

(51) Int. Cl.
 *A61B 5/1455* (2006.01)
 *A61B 5/145* (2006.01)
 *A61B 5/1459* (2006.01)

(52) U.S. Cl.
 CPC .... *A61B 5/14532* (2013.01); *G01N 2201/068* (2013.01); *G01N 2201/06113* (2013.01); *G01N 2201/12* (2013.01)

(58) Field of Classification Search
 CPC ....... A61B 5/1459; A61B 5/72; A61B 5/7203; A61B 5/7214; G01N 21/00; G01N 21/658; G01N 2201/12; G01N 2201/068; G01N 2201/06113
 See application file for complete search history.

(56) References Cited

U.S. PATENT DOCUMENTS

| | | | |
|---|---|---|---|
| 2004/0023317 A1* | 2/2004 | Motamedi | A61B 5/14532 435/14 |
| 2007/0134805 A1* | 6/2007 | Gilbert | G01N 21/658 436/164 |
| 2008/0214913 A1* | 9/2008 | Van Gogh | A61B 5/14532 600/318 |
| 2009/0118605 A1* | 5/2009 | Van Duyne | A61B 5/14532 600/365 |
| 2009/0273780 A1 | 11/2009 | Tomaru et al. | |
| 2010/0167416 A1 | 7/2010 | Kabilan et al. | |
| 2011/0004076 A1 | 1/2011 | Janna et al. | |
| 2011/0118570 A1* | 5/2011 | Pedersen | A61B 5/14532 600/316 |

FOREIGN PATENT DOCUMENTS

| | | |
|---|---|---|
| JP | 2009-103651 A | 5/2009 |
| JP | 2009-526965 A | 7/2009 |
| JP | 2009-270852 A | 11/2009 |
| JP | 2011-514812 A | 5/2011 |
| JP | 2013-205078 A | 10/2013 |
| WO | 2004-075032 A2 | 9/2004 |
| WO | 2006-090308 A1 | 8/2006 |
| WO | 2006-098813 A1 | 9/2006 |
| WO | 2011-053247 A1 | 5/2011 |

* cited by examiner

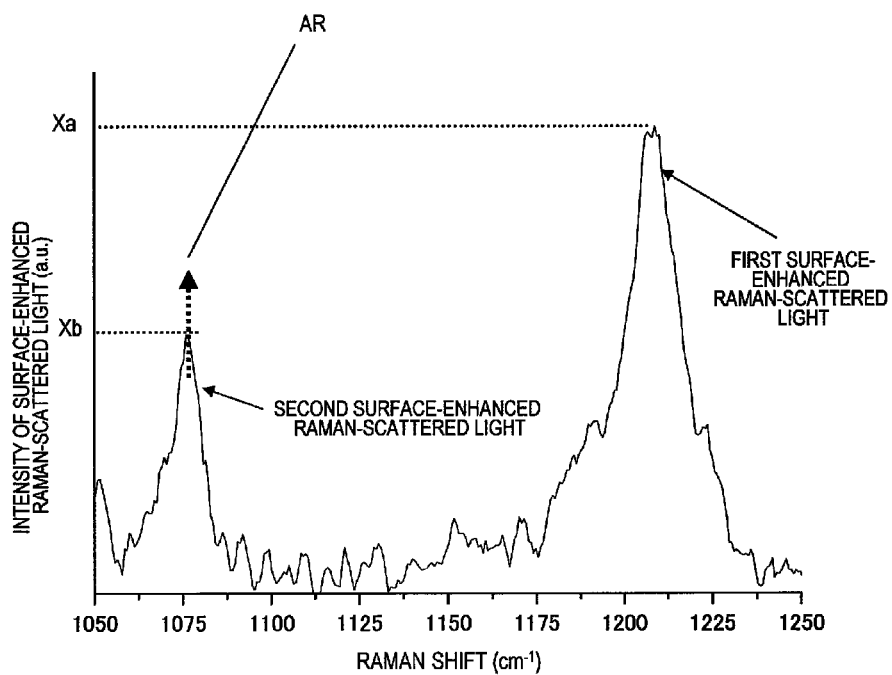

METHOD AND DETECTION SYSTEM FOR DETECTING AN ANALYTE

This is a continuation of International Application No. PCT/JP2013/007312, with an international filing date of Dec. 12, 2013, which claims priority of Japanese Patent Application No. 2012-284183, filed on Dec. 27, 2012, the contents of which are hereby incorporated by reference.

BACKGROUND

1. Technical Field

The present application relates to a method for detecting an analyte and a detection system that are based on surface-enhanced Raman spectroscopy.

2. Description of the Related Art

In Raman spectroscopy, a substance is irradiated with monochromatic light (excitation light) of a certain frequency so that scattered light occurs therefrom, and any scattered light that has a different frequency (hereinafter referred to as Raman-scattered light) from the frequency of the incident light is spectropically detected. A difference (Raman shift) between the frequency of the Raman-scattered light and the frequency of the incident light is equal to the frequency which corresponds to the difference between energy levels of vibration or rotation of molecules and atoms in the molecule or crystal that composes a substance, and takes a value which is specific to the structure of the substance. Therefore, Raman spectroscopy is utilized to discover the structure and state of a molecule.

Among other Raman spectroscopy techniques, surface-enhanced Raman spectroscopy has been proposed, which utilizes surface-enhanced Raman scattering (SERS).

Surface-enhanced Raman scattering is a phenomenon in which Raman-scattered light from molecules that have adhered to the surface of a specially-designed sensor chip having a precious metal structure of nanometer size increases in intensity. Surface-enhanced Raman scattering provides an enhancement of usually about $10^4$ to $10^9$. This enables highly sensitive detection of molecules which are immobilized on a metal surface, or even molecules near the metal surface.

In the field of medical diagnosis, a wide range of applications of surface-enhanced Raman spectroscopy is being considered. Surface-enhanced Raman spectroscopy is especially applied to the detection of biological components such as glucose that is contained in a biological body. Furthermore, based on an intensity of surface-enhanced Raman-scattered light, the concentration of a biological component can be calculated.

International Publication No. 2006/090308 discloses a method of measuring the glucose concentration in a biological body. According to International Publication No. 2006/090308, a sensor chip is embedded near capillary blood vessels, and the intensity of surface-enhanced Raman-scattered light that may occur is measured, whereby the scattering effect of erythrocytes existing in the blood and the interference effects of signals from other components can be reduced. This enables detection of surface-enhanced Raman-scattered light with a good SN ratio.

SUMMARY

However, the intensity of surface-enhanced Raman-scattered light from an analyte such as glucose is affected by the measurement environment (e.g., the refractive index around the sensor chip, the irradiation angle of excitation light, the intensity of excitation light that is radiated).

When chronologically detecting or quantitatively evaluating an analyte such as glucose within a biological body or a subject solution, the refractive index around the sensor chip, and/or the irradiation angle or the intensity of excitation light may vary. For this reason, accurate quantitative evaluation has been very difficult with conventional methods.

One non-limiting, and exemplary embodiment of the present application provides a detection method and detection system for an analyte based on surface-enhanced Raman spectroscopy, which allows an analyte such as glucose to be detected with a high precision even in an environment that undergoes changes in the measurement environment, e.g., in vivo.

In one general aspect, a method for detecting an analyte disclosed herein comprises the following steps (a), (b), (c), (d), and (e): step (a) of providing a detection apparatus, the detection apparatus including a light source and detection means; step (b) of irradiating a sensor chip with excitation light from the light source to generate first surface-enhanced Raman-scattered light having a first peak and second surface-enhanced Raman-scattered light having a second peak different from the first peak, the sensor chip including a substrate, a metal pattern formed on a side of the substrate that is irradiated with the excitation light, and a first substance and a second substance provided near the metal pattern, wherein, the first substance generates the first surface-enhanced Raman-scattered light; a first intensity Xa which is an intensity of the first surface-enhanced Raman-scattered light does not vary with changes in the concentration of the analyte; the second substance generates the second surface-enhanced Raman-scattered light; and a second intensity Xb which is an intensity of the second surface-enhanced Raman-scattered light varies with changes in the concentration of the analyte; step (c) of detecting the first surface-enhanced Raman-scattered light from the first substance with the detection means to obtain the first intensity Xa; step (d) of detecting the second surface-enhanced Raman-scattered light from the second substance with the detection means to obtain the second intensity Xb; and step (e) of calculating a value Xc resulting from dividing the second intensity Xb with the first intensity Xa.

According to the above aspect, an analyte that is contained in a biological body or a subject solution (e.g., a biological component such as glucose) can be detected more accurately.

These general and specific aspects may be implemented using a system, a method, and a computer program, and any combination of systems, methods, and computer programs.

Additional benefits and advantages of the disclosed embodiments will be apparent from the specification and Figures. The benefits and/or advantages may be individually provided by the various embodiments and features of the specification and drawings disclosure, and need not all be provided in order to obtain one or more of the same.

BRIEF DESCRIPTION OF THE DRAWINGS

FIG. 4B is another exemplary spectrum chart showing first and second surface-enhanced Raman-scattered light.

DETAILED DESCRIPTION

Figure 1:
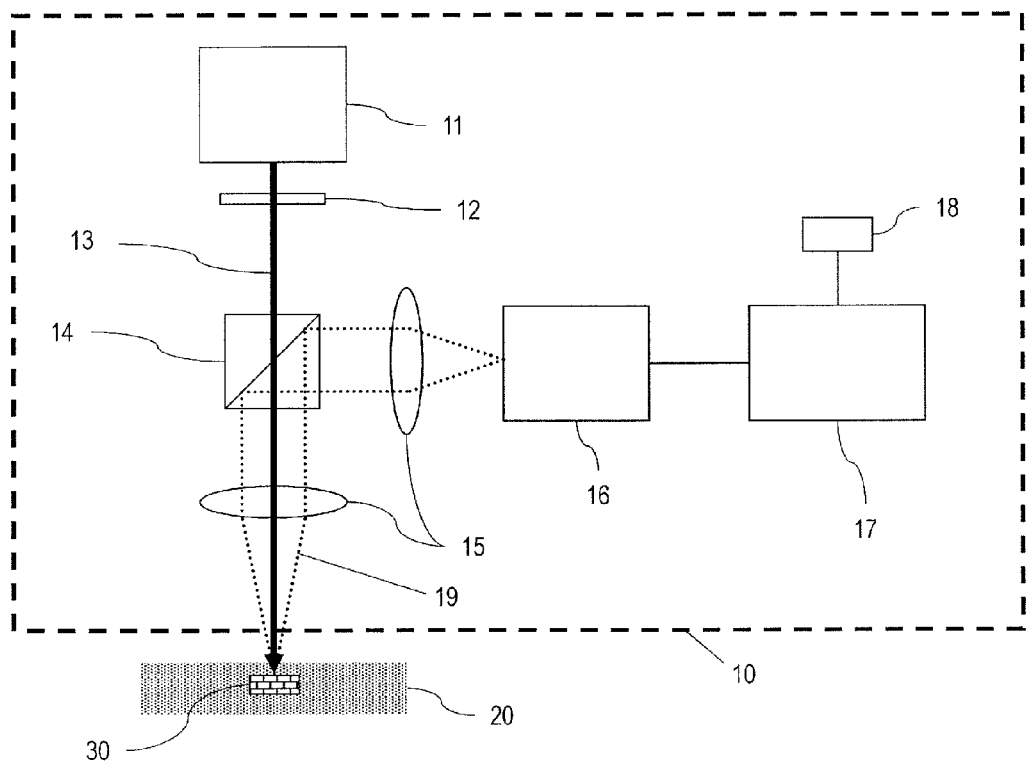
FIG. 1 is a diagram showing a detection apparatus according to an illustrative embodiment.

First, one implementation of the present disclosure will be described in outline.

A method as one implementation of the present disclosure is a method for detecting an analyte, comprising the following steps (a), (b), (c), (d), and (e):
step (a) of providing a detection apparatus,
the detection apparatus including a light source and detection means;
step (b) of irradiating a sensor chip with excitation light from the light source to generate first surface-enhanced Raman-scattered light having a first peak and second surface-enhanced Raman-scattered light having a second peak different from the first peak,
the sensor chip including
a substrate,
a metal pattern formed on a side of the substrate that is irradiated with the excitation light, and
a first substance and a second substance provided near the metal pattern, wherein,
the first substance generates the first surface-enhanced Raman-scattered light;
a first intensity Xa which is an intensity of the first surface-enhanced Raman-scattered light does not vary with changes in the concentration of the analyte;
the second substance generates the second surface-enhanced Raman-scattered light; and
a second intensity Xb which is an intensity of the second surface-enhanced Raman-scattered light varies with changes in the concentration of the analyte;
step (c) of detecting the first surface-enhanced Raman-scattered light from the first substance with the detection means to obtain the first intensity Xa;
step (d) of detecting the second surface-enhanced Raman-scattered light from the second substance with the detection means to obtain the second intensity Xb; and
step (e) of calculating a value Xc resulting from dividing the second intensity Xb with the first intensity Xa.

The detection apparatus may include a memory retaining information indicating correlation between the value Xc and the concentration of the analyte; and step (e) may calculate the concentration of the analyte based on the value Xc and the information.

The sensor chip may be embedded in a biological body; and the concentration of the analyte contained in the biological body may be calculated.

In any of the above methods, the analyte may be glucose.

The first substance may be monochloro-para-xylylene polymer; and the second substance may be 4-mercaptophenylboronic acid.

The first peak of the first surface-enhanced Raman-scattered light may be at 1209 $cm^{-1}$; and the second peak of the second surface-enhanced Raman-scattered light may be at 1076 $cm^{-1}$.

A detection system as another implementation of the present disclosure is a detection system for detecting an analyte, comprising: a detection apparatus, and a sensor chip,
the detection apparatus including a light source and detection means, wherein
the sensor chip includes
a substrate,
a metal pattern formed on a side of the substrate that is irradiated with excitation light from the light source, and
a first substance and a second substance provided near the metal pattern;
the first substance generates first surface-enhanced Raman-scattered light having a first peak;
a first intensity Xa which is an intensity of the first surface-enhanced Raman-scattered light does not vary with changes in the concentration of the analyte;
the second substance generates second surface-enhanced Raman-scattered light having a second peak different from the first peak;
a second intensity Xb which is an intensity of the second surface-enhanced Raman-scattered light varies with changes in the concentration of the analyte; and
the detection system
irradiates the sensor chip with the excitation light to generate the first surface-enhanced Raman-scattered light and the second surface-enhanced Raman-scattered light,
detects the first surface-enhanced Raman-scattered light from the first substance with the detection means to obtain the first intensity Xa,
detects the second surface-enhanced Raman-scattered light from the second substance with the detection means to obtain the second intensity Xb, and
calculates a value Xc resulting from dividing the second intensity Xb with the first intensity Xa.

The detection apparatus may include a memory retaining information indicating correlation between the value Xc and the concentration of the analyte; and the detection system may calculate the concentration of the analyte based on the value Xc and the information.

The sensor chip may be embedded in a biological body; and the detection system may calculate the concentration of the analyte contained in the biological body.

In any of the above detection systems, the analyte may be glucose.

The first substance may be monochloro-para-xylylene polymer; and the second substance may be 4-mercaptophenylboronic acid.

The first peak of the first surface-enhanced Raman-scattered light may be at 1209 $cm^{-1}$; and the second peak of the second surface-enhanced Raman-scattered light may be at 1076 $cm^{-1}$.

A method of controlling a detection system as still another implementation of the present disclosure is a method of controlling a detection system for detecting an analyte,
the detection system including a detection apparatus and a sensor chip,
the detection apparatus including a light source and detection means,
the sensor chip including
a substrate,
a metal pattern formed on a side of the substrate that is irradiated with excitation light from the light source, and a first substance and a second substance provided near the metal pattern, wherein, the first substance generates first surface-enhanced Raman-scattered light having a first peak;

a first intensity Xa which is an intensity of the first surface-enhanced Raman-scattered light does not vary with changes in the concentration of the analyte;

the second substance generates second surface-enhanced Raman-scattered light having a second peak different from the first peak; and a second intensity Xb which is an intensity of the second surface-enhanced Raman-scattered light varies with changes in the concentration of the analyte, the method comprising:

a step of irradiating the sensor chip with the excitation light from the light source to generate the first surface-enhanced Raman-scattered light and the second surface-enhanced Raman-scattered light;

a step of detecting the first surface-enhanced Raman-scattered light from the first substance with the detection means to obtain the first intensity Xa;

a step of detecting the second surface-enhanced Raman-scattered light from the second substance with the detection means to obtain the second intensity Xb; and a step of calculating a value Xc resulting from dividing the second intensity Xb with the first intensity Xa.

Hereinafter, embodiments of the present disclosure will be described with reference to the drawings.

Embodiment 1

Embodiment 1 will be described with reference to FIGS. 1 to 5. The component elements shown in the figures are not necessary drawn to scale, but may be exaggerated in order to clearly illustrate the principles of the present invention.

The present embodiment proposes a method of detecting an analyte (e.g., a biological component such as glucose) that is contained in a biological body (e.g., a human) or a subject solution.

Figure 5:
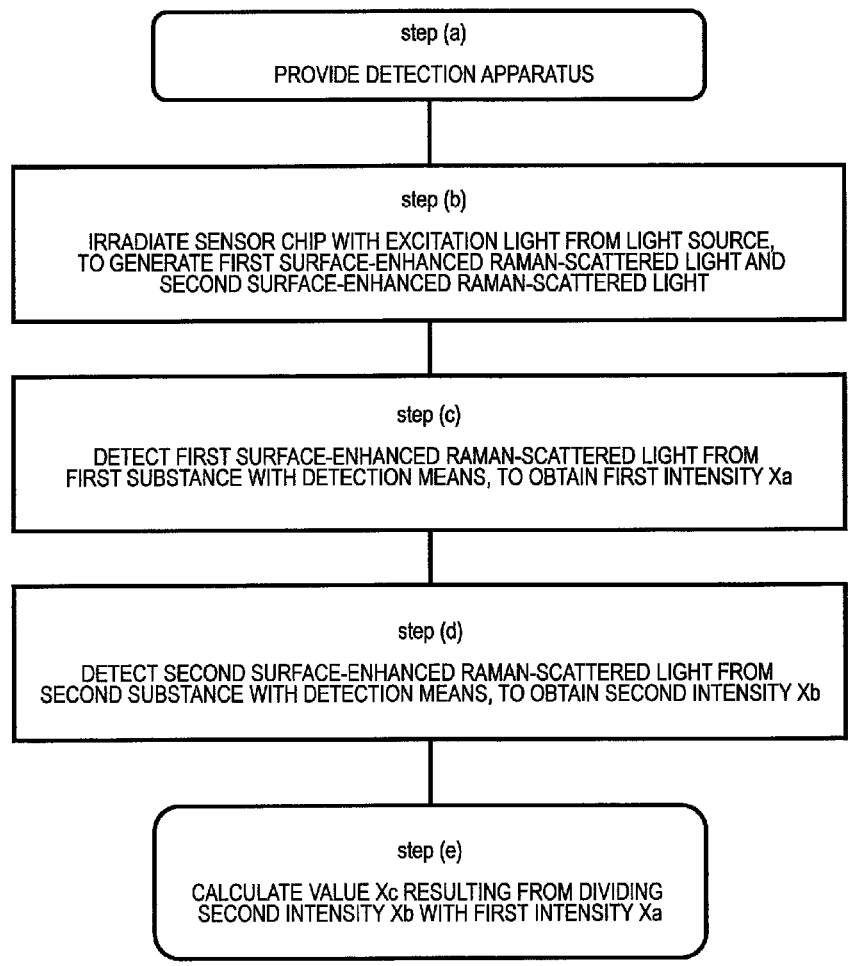
FIG. 5 is an exemplary flowchart of a detection method according to Embodiment 1.

FIG. 5 is an exemplary flowchart of the detection method according to Embodiment 1. The detection method according to Embodiment 1 includes steps (a) to (e) described below.

Step (a)

Step (a) is a step of providing a detection apparatus. A detection apparatus 10 shown in FIG. 1 includes a light source 11 and a detection means. The detection apparatus 10 includes a spectrometer 16 as one example of the detection means.

As necessary, the detection apparatus 10 includes a bandpass filter 12, an optical system 15, a beam splitter 14, a memory 18, and a calculation section 17.

Excitation light 13 from the light source 11 is substantially parallel light having a wavelength of 785 nm, for example. An example of the substantially parallel light is light having a circular beam shape with a diameter of 100 micrometers.

The bandpass filter 12 only allows the excitation light 13 from the light source 11 to pass therethrough.

The optical system 15 shapes the surface-enhanced Raman-scattered light occurring from a sensor chip 30 into a beam. The optical system 15 may include one or more lenses.

The beam splitter 14 allows surface-enhanced Raman-scattered light 19 occurring from the sensor chip 30 to be led into the spectrometer 16.

The spectrometer 16, which exemplifies the detection means, detects the surface-enhanced Raman-scattered light 19. The spectrometer 16 outputs a signal which is in accordance with the detected light. The spectrometer 16 may have a plurality of photosensitive regions.

The calculation section 17 (e.g., a computer) calculates the intensity of the light which is detected by the spectrometer 16. From the calculated intensity, it calculates the concentration of the analyte, for example.

Step (b)

Step (b) is a step of irradiating the sensor chip with excitation light from the light source to generate first surface-enhanced Raman-scattered light and second surface-enhanced Raman-scattered light.

The sensor chip includes a substrate, a metal pattern formed on a side of the substrate that is irradiated with excitation light, and a first substance and a second substance provided near the metal pattern.

The first substance generates first surface-enhanced Raman-scattered light having a first peak. A first intensity Xa, which is an intensity of the first surface-enhanced Raman-scattered light, does not vary with changes in the concentration of the analyte.

The second substance generates second surface-enhanced Raman-scattered light having a second peak different from the first peak. A second intensity Xb, which is an intensity of the second surface-enhanced Raman-scattered light, varies with changes in the concentration of the analyte.

Hereinafter, step (b) according to Embodiment 1 will be described in detail.

In Embodiment 1, glucose will be illustrated as the analyte. Monochloro-para-xylylene polymer and 4-mercaptophenylboronic acid (4MPBA) will be illustrated as the first substance and the second substance, respectively. In an example described below, a sensor chip 30 is embedded in a biological body.

At step (b), excitation light 13 from the light source 11 is transmitted through the biological body surface (skin). When irradiated with the transmitted excitation light, the sensor chip 30 which is embedded in the biological body (e.g., skin) generates surface-enhanced Raman-scattered light 19. The surface-enhanced Raman-scattered light 19 contains first surface-enhanced Raman-scattered light and second surface-enhanced Raman-scattered light.

Figure 2:
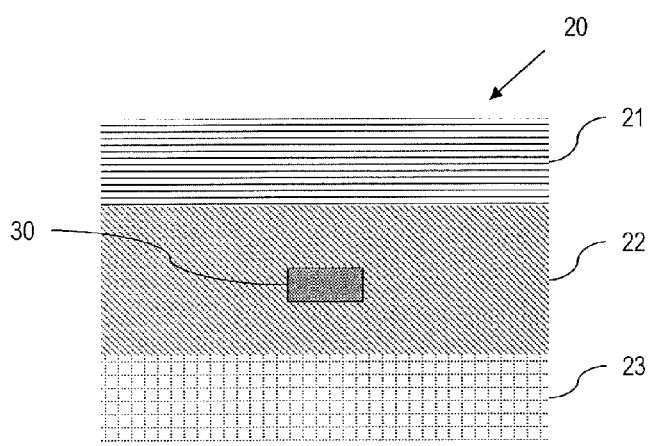
FIG. 2 is a schematic cross-sectional view of skin tissue.

FIG. 2 schematically shows an enlarged cross-sectional view of skin tissue 20. As shown in FIG. 2, the skin tissue 20 includes epidermal tissue 21, dermis tissue 22, and subcutaneous tissue 23. The epidermal tissue 21, dermis tissue 22, and subcutaneous tissue 23 are layered in this order. The epidermal tissue 21 is located at the surface of the biological body. The epidermal tissue 21 has a thickness of approximately 0.2 mm to 0.5 mm. The dermis tissue 22 has a thickness of approximately 0.5 mm to 2 mm. The sensor chip 30 is embedded in the dermis tissue 22, for example. The sensor chip 30 is retained in a manner of being immersed in the interstitial fluid, which is a bodily fluid existing between tissue cells. The subcutaneous tissue 23 is mainly composed of fat tissue. The term "bodily fluid" used in the present specification means an interstitial fluid.

The dermis tissue 22 includes plural capillary blood vessels. Therefore, bodily fluids contain biological components from the capillary blood vessels. In particular, the walls of capillary blood vessels have a high permeability with respect to glucose. Therefore, a glucose concentration in the bodily fluid is highly correlated with the blood glucose level.

As shown in FIG. 2, the sensor chip 30 is embedded in the dermis tissue 22 so that its face having the metal pattern (e.g., metal particles 34 as will be described later) thereon lies parallel to the epidermal tissue 21. The distance from the epidermal tissue 21 to the sensor chip 30 is approximately 1.5 mm.

An example of a construction of the sensor chip according to an embodiment of the present disclosure will be described with reference to FIG. 3.

In an embodiment of the present disclosure, there is no particular limitation as to the substrate 31 so long as it is a substrate which allows an analyte to be detected through surface-enhanced Raman spectroscopy. For example, the substrate 31 may a solid substrate. Herein, glass, plastic, silicon, or the like is used, which are inexpensive and readily available. The substrate 31 has a diameter of approximately 1 mm and a thickness of approximately 0.1 to 0.5 mm, for example.

On at least one face of the substrate 31, a layer 33 of monochloro-para-xylylene polymer (hereinafter referred to as parylene C) serving as the first substance is formed. The face of the substrate on which the parylene C layer 33 is formed is the face that is irradiated with excitation light.

The parylene C layer 33 may be formed by chemical vapor deposition (CVD). By forming the parylene C layer 33 by chemical vapor deposition, it becomes possible to uniformize the coating film thickness or reduce the film thickness (e.g., 0.05 to 25 µm), as compared to coating techniques by spraying or dip coating. Furthermore, even in a construction with a reduced coating film thickness, the parylene C layer 33 is unlikely to suffer from pinholes.

Since the sensor chip is to be embedded in a biological body, coating with a polymer which has low bioactivity may be provided around the sensor chip. This confers biocompatibility to the sensor chip, and precludes (or minimizes) interactions of nonspecific proteins with the chip surface as well as inflammatory responses. Parylene C provides a surface which is poorly biologically active, thus permitting embedding of the sensor chip into a biological body.

The metal particles 34 (an example of the metal pattern) are formed on the parylene C layer 33. There is no particular limitation as to the metal particles 34, so long as it is made of a substance that exhibits a plasmon. As the metal particles 34, precious metals alone, e.g., Au, Ag, Cu, or Pt, or an intermetallic compound, alloy, or the like that is composed of such elements, can be used.

Although there is no particular limitation as to the diameter of the metal particles, about 100 nm is advantageous. The thickness of the metal particles (metal pattern) along the thickness direction of the substrate may be in a range of 10 to 200 nm. In the case of Au, the thickness of the metal particles (metal pattern) along the thickness direction of the substrate is about 50 nm, for example. The metal particles 34 may be formed through patterning by using a lithography technique or imprint technique.

The metal particles 34 are modified with 4-mercaptophenylboronic acid 35, which includes a boronic acid group that is capable of binding to glucose. That is, on the metal pattern, a film of 4-mercaptophenylboronic acid as the second substance is formed.

The sensor chip 30 may include a layer of biocompatible polymer. The biocompatible polymer 32 shown in FIG. 3 may contain polydimethylsiloxane (PDMS), parylene C, parylene HT, polycarbonate, polyolefin, polyurethane, acrylonitrile copolymer, a copolymer of polyvinyl chloride, polyamide, polysulfone, polystyrene, vinyl fluoride resin, polyvinyl alcohol, polyvinyl ester, polyvinyl butyrate, polyvinyl acetate, polyvinylidene chloride, polyvinylidene fluoride, polyimide, polyisoprene, polyisobutylene, polybutadiene, polyethylene, polyether, polytetrafluoroethylene, polychloroether, polymethyl methacrylate, polybutylmethacrylate, nylon, cellulose, gelatin, or silicone rubber, although this is not a limitation.

Note that the metal pattern is not limited to particle shapes alone. The metal pattern may be gold nanorods, or a metal film having minute protrusions and depressions, for example. The metal pattern may be any structure that exhibits surface-enhanced Raman scattering.

Note that the first substance is not limited to monochloro-para-xylylene polymer alone. The first substance may be any substance the intensity of whose surface-enhanced Raman-scattered light does not vary with changes in the concentration of the analyte.

Note that the second substance is not limited to 4-mercaptophenylboronic acid alone. The second substance may be any substance the intensity of whose surface-enhanced Raman-scattered light varies with changes in the concentration of the analyte. At the same time, the second substance may be any substance that generates surface-enhanced Raman-scattered light having a peak different from the peak of surface-enhanced Raman-scattered light from the first substance.

The sensor chip may alternatively have the following construction.

Figure 6:
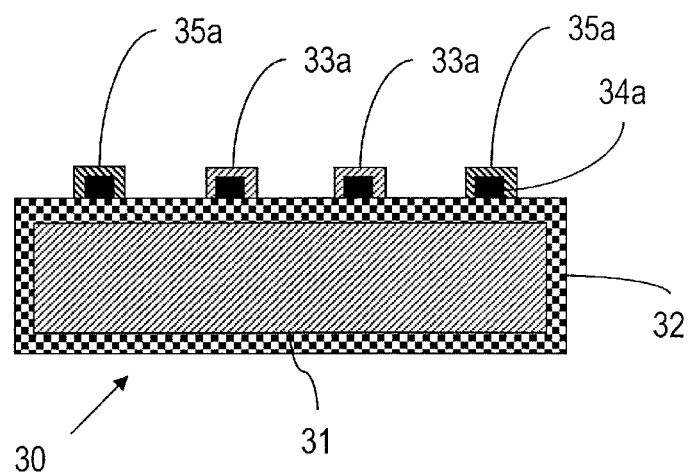
FIG. 6 is a diagram schematically showing another exemplary construction for a sensor chip.

FIG. 6 is a diagram schematically showing another exemplary construction for the sensor chip. As shown in FIG. 6, the first substance 33a may be provided on portions of the metal pattern 34a, while the second substance 35a may be provided on other portions of the metal pattern 34a.

Figure 3:
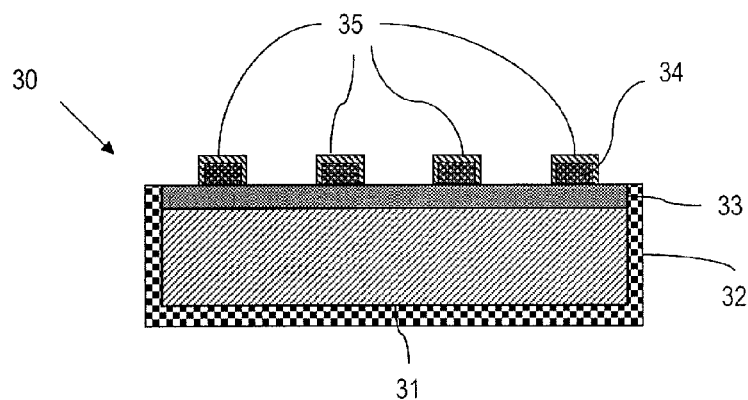
FIG. 3 is a diagram schematically showing a sensor chip according to an illustrative embodiment.

The sensor chip construction is not limited the constructions shown in FIG. 3 and FIG. 6 alone. The sensor chip may be of any construction that includes a substrate, a metal pattern formed on a side of the substrate that is irradiated with excitation light, and a first substance and a second substance provided near the metal pattern.

Step (c) and Step (d)

Step (c) is a step of detecting first surface-enhanced Raman-scattered light from the first substance with the detection means to obtain a first intensity Xa. Step (d) is a step of detecting second surface-enhanced Raman-scattered light from the second substance with the detection means to obtain a second intensity Xb.

As shown in FIG. 1, when the sensor chip 30 is irradiated with excitation light 13 from the light source 11, a surface plasmon resonance occurs around the metal particles 34, whereby the electric field in the vicinity of the metal particles 34 is enhanced. This causes enhancement of Raman-scattered light from any substance that is located in the vicinity of the metal particles 34 (within 0.5 to 30 nm).

The surface-enhanced Raman-scattered light 19 is shaped by the optical system (optical lens system) 15, reflected by the beam splitter 14, and subjected to further shaping by the optical system (optical lens system) 15, and thereafter detected by the spectrometer 16.

As the spectrometer 16, any known technique can be used without limitation, e.g., Czerny-Turner spectrographs, Echelle spectrographs, flat-field spectrographs, and filter spectrographs.

As described earlier, the intensity of surface-enhanced Raman-scattered light is $10^4$ to $10^9$ times greater than the intensity of usual Raman-scattered light. Therefore, the surface-enhanced Raman-scattered light that occurs in the vicinity of the metal particles 34 has a far greater intensity than that of Raman-scattered light occurring in skin tissue (epidermal tissue 21, dermis tissue 22). This means that Raman-scattered light from the vicinity of the metal particles 34 is selectively enhanced.

Figure 4A:
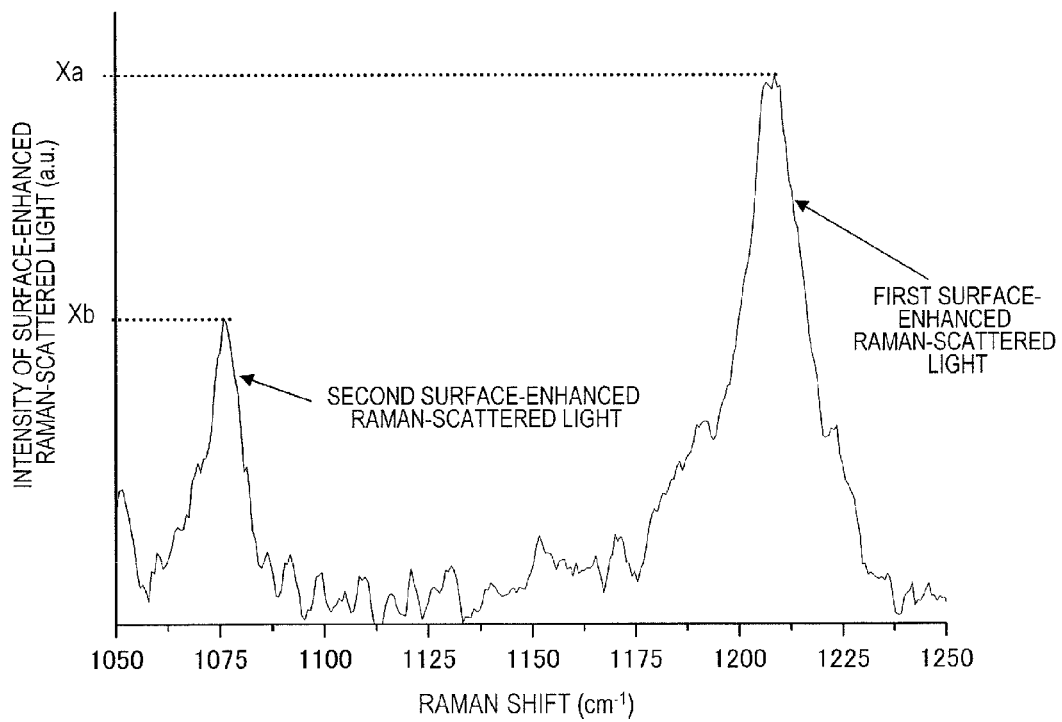
FIG. 4A is an exemplary spectrum chart showing first and second surface-enhanced Raman-scattered light.

FIG. 4A shows an exemplary spectrum chart of first and second surface-enhanced Raman-scattered light in the case where no analyte (e.g., glucose) exists.

As shown in FIG. 4A, a peak of first surface-enhanced Raman-scattered light occurs at 1209 cm$^{-1}$, which originates in the benzene rings included in the monochloro-para-xylylene polymer as the first substance located in the vicinity of the metal particles 34. The signal intensity (e.g., intensity at the peak position) of first surface-enhanced Raman-scattered light is indicated as Xa. In other words, a first intensity Xa is obtained by detecting first surface-enhanced Raman-scattered light from the first substance with the detection means.

Similarly, a peak of second surface-enhanced Raman-scattered light occurs at 1076 cm$^{-1}$, which originates in the benzene ring included in 4-mercaptophenylboronic acid as the second substance located in the vicinity of the metal particles 34. The signal intensity (e.g., intensity at the peak position) of second surface-enhanced Raman-scattered light is indicated as Xb. In other words, a second intensity Xb is obtained by detecting second surface-enhanced Raman-scattered light from the second substance with the detection means.

In the case where the first substance is monochloro-para-xylylene polymer and the second substance is 4-mercaptophenylboronic acid, the aforementioned two kinds of surface-enhanced Raman-scattered light (first and second surface-enhanced Raman-scattered light) are both surface-enhanced Raman-scattered light which originates in a benzene ring. Therefore, the two kinds of surface-enhanced Raman-scattered light both have a sharp peak, and provide a high intensity signal. Furthermore, although both peaks similarly originate in a benzene ring, these peaks do not overlap in the range shown in FIG. 4A.

As indicated in International Publication No. 2011/053247, when glucose is bound to a phenylboronic acid compound or a derivative thereof, a change occurs in the intensity of surface-enhanced Raman-scattered light due to electronic and/or steric changes.

In other words, when an analyte (which herein is glucose) binds to a second substance (which herein is 4-mercaptophenylboronic acid), the intensity of second surface-enhanced Raman-scattered light from the second substance changes. As schematically shown in FIG. 4B by a broken-lined arrow AR, when the analyte (e.g., glucose) exists, the second surface-enhanced Raman-scattered light is enhanced.

In other words, the second intensity Xb, i.e., the intensity of second surface-enhanced Raman-scattered light, varies with changes in the glucose concentration within the biological body.

On the other hand, the first intensity Xa, i.e., the intensity of the first surface-enhanced Raman-scattered light, does not vary with changes in the glucose concentration within the biological body.

Note that the intensity of surface-enhanced Raman-scattered light greatly varies with changes in the measurement environment. Changes in the measurement environment may be, for example, changes in the refractive index around the sensor chip, changes in the irradiation angle of excitation light, or changes in the intensity of excitation light that is radiated. For example, when laser irradiation (excitation light irradiation) is performed into a biological body, it is difficult to fix the laser irradiation angle.

Therefore, if the measurement environment changes from measurement to measurement, the intensity Xa of first surface-enhanced Raman-scattered light and the intensity Xb of second surface-enhanced Raman-scattered light will vary.

However, the intensity ratio Xc therebetween (Xc=Xb/Xa) will not be affected by the measurement environment, but will always stay constant. In other words, the intensity ratio Xc (Xc=Xb/Xa) does not vary with changes in the measurement environment.

For this reason, first surface-enhanced Raman-scattered light, which is unaffected by the concentration of the analyte (e.g., glucose), is used as reference light, and furthermore the intensity ratio Xc, which is unaffected by the measurement environment, is used. This enables detection or quantitative measurement of the analyte (e.g., glucose) while reducing the influences of changes in the measurement environment.

In the case where obstructing components such as proteins in the biological body exist in the vicinity of the metal particles 34, surface-enhanced Raman-scattered light (hereinafter referred to as obstructing Raman-scattered light) will similarly occur from the obstructing components. However, when the analyte is glucose, the first substance is monochloro-para-xylylene polymer, and the second substance is 4-mercaptophenylboronic acid, no peaks of obstructing Raman-scattered light will exist in regions near the peak positions of first surface-enhanced Raman-scattered light and second surface-enhanced Raman-scattered light. Thus, glucose detection errors associated with obstructing components can be reduced.

Step (e)

Step (e) is a step of calculating a value Xc resulting from dividing the second intensity Xb with the first intensity Xa. The calculation section 17 calculates a ratio Xc (Xc=Xb/Xa) between the first surface-enhanced Raman-scattered light intensity (Xa) and the second surface-enhanced Raman-scattered light intensity (Xb) as detected by the spectrometer 16. Based on the value Xc, the calculation section 17 outputs a detection result as to the presence or absence of the analyte.

Thereafter, the calculation section 17 may calculate the concentration of the analyte based on information indicating correlation between the peak intensity ratio Xc and the concentration of the analyte (e.g., glucose). This enables a more accurate measurement of the concentration of the analyte (e.g., glucose) in which the influences of changes in the measurement environment are reduced.

The information indicating correlation between the peak intensity ratio Xc and the concentration of the analyte may be a calibration curve, for example. In this case, by using the peak intensity ratio Xc as an input value, the calculation section 17 may calculate a concentration value of the analyte that corresponds to the input value Xc through a mathematical function representing the calibration curve.

In advance, the detection apparatus 10 may retain information indicating correlation between the peak intensity ratio Xc and the concentration of the analyte, in the memory 18. For example, the detection apparatus 10 may retain parameters of a mathematical function representing the calibration curve, etc., in advance in the memory 18.

The peak intensity ratio Xc is constant across environments with different refractive index distributions around the sensor chip, or different irradiation angles of excitation light or irradiation conditions. It is by way of the presence or absence of the analyte (e.g., glucose), or differences in concentration, that the peak intensity ratio Xc shows a different value.

Figure 8:
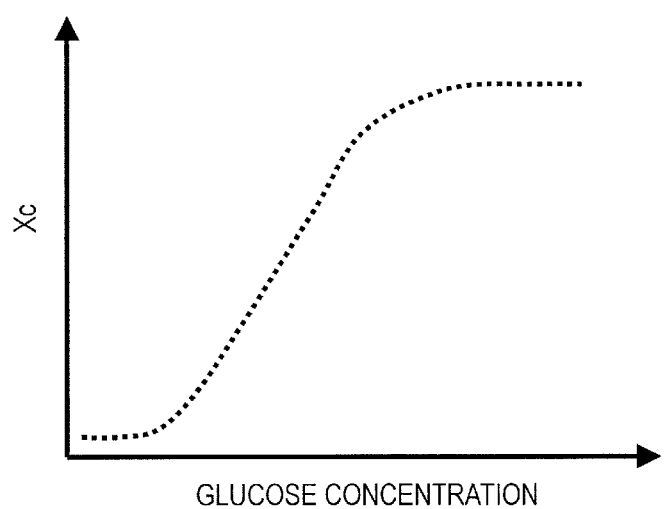
FIG. 8 is a diagram showing an exemplary relationship between the glucose concentration and the peak intensity ratio Xc.

FIG. 8 is a diagram showing an exemplary relationship between the glucose concentration and the peak intensity ratio Xc. As shown in FIG. 8, the peak intensity ratio Xc becomes more enhanced with glucose concentration.

Note that a calibration curve may be acquired through the following procedure, for example.

Subject solutions containing the analyte in various concentrations are prepared. In these subject solutions, the solvent is pure water, while the solute is the analyte. For each of the plurality of subject solutions with known concentrations of analyte, surface-enhanced Raman scattering intensities Xa and Xb are measured. Thereafter, a ratio Xc (Xc=Xb/Xa) between these two specific peak intensities is calculated. This is plotted against the vertical axis representing the intensity ratio Xc of surface-enhanced Raman-scattered light and the horizontal axis representing the concentration of analyte. A calibration curve is obtained by determining a mathematical function which approximates a graph that is obtained by connecting the plurality of coordinates.

Thus, by using the detection method according to Embodiment 1, it also becomes possible to measure the concentration of the analyte (e.g., glucose) that exists in the biological body. The aforementioned steps may be executed through control on the basis of instructions from the calculation section 17.

In Embodiment 1, the sensor chip may be placed in the subject solution. In this case, the detection method according to Embodiment 1 may detect the analyte as being contained in the subject solution. In this context, the subject solution may be a fluid which is extracted from a biological body. The subject solution may be, for example, blood, sweat, tears, urine, saliva, or the like.

Embodiment 2

Figure 7:
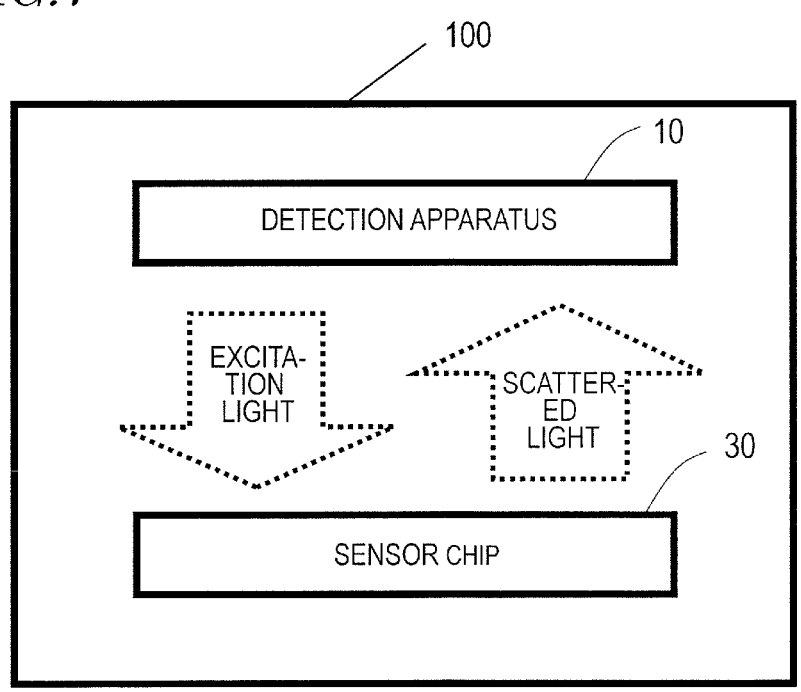
FIG. 7 is a diagram schematically showing a detection system according to Embodiment 2.

FIG. 7 shows an exemplary construction for a detection system according to Embodiment 2 which detects an analyte (e.g., a biological component such as glucose) that is contained in a biological body (e.g., a human) or a subject solution. By being controlled with the detection method which has been described in Embodiment 1, the detection system according to Embodiment 2 detects an analyte.

The detection system 100 of Embodiment 2 includes a detection apparatus 10 and a sensor chip 30. The detection apparatus 10 and the sensor chip 30 have already been described in Embodiment 1.

That is, the detection system according to Embodiment 2 is a detection system which measures the concentration of an analyte, for example, including a detection apparatus and a sensor chip. The detection apparatus includes a light source and a detection means. The sensor chip includes a substrate, a metal pattern formed on a side of the substrate that is irradiated with excitation light from the light source, and a first substance and a second substance provided near the metal pattern. The first substance generates first surface-enhanced Raman-scattered light having a first peak. A first intensity Xa, which is an intensity of the first surface-enhanced Raman-scattered light, does not vary with changes in the concentration of the analyte. The second substance generates second surface-enhanced Raman-scattered light having a second peak different from the first peak. A second intensity Xb, which is an intensity of the second surface-enhanced Raman-scattered light, varies with changes in the concentration of the analyte. The detection system irradiates the sensor chip with excitation light to generate first surface-enhanced Raman-scattered light and second surface-enhanced Raman-scattered light. First surface-enhanced Raman-scattered light from the first substance is detected with the detection means to obtain a first intensity Xa. Second surface-enhanced Raman-scattered light from the second substance is detected with the detection means to obtain a second intensity Xb. Then, a value Xc resulting from dividing the second intensity Xb with the first intensity Xa is calculated.

With the above construction, it is possible to reduce the influences of changes in the measurement environment (e.g., changes in the refractive index around the sensor chip, changes in the irradiation angle of excitation light, or changes in the intensity of excitation light that is radiated). As a result, an analyte that is contained in a biological body or a subject solution (e.g., a biological component such as glucose) can be detected more accurately.

In the detection system 100 of Embodiment 2, the detection apparatus 10 may include a memory which retains information indicating correlation between the peak intensity ratio Xc and the concentration of the analyte. In this case, the detection system 100 may calculate a concentration of the analyte based on the peak intensity ratio Xc and this information. This enables a more accurate measurement of the concentration of the analyte (e.g., glucose) in which the influences of changes in the measurement environment are reduced. Note that the information indicating correlation between the peak intensity ratio Xc and the concentration of the analyte may be a calibration curve.

In the detection system 100 of Embodiment 2, the sensor chip 30 may be embedded in a biological body. In this case, the detection system 100 of Embodiment 2 may detect an analyte that is contained in the biological body.

Alternatively, the sensor chip may be placed in a subject solution. In this case, the detection system may detect an analyte that is contained in the subject solution. In this context, the subject solution may be a fluid which has been extracted from a biological body. For example, the subject solution may be blood, sweat, tears, urine, saliva, or the like.

In the detection system according to Embodiment 2, the analyte may be glucose. In this case, the first substance may be monochloro-para-xylylene polymer. Furthermore, the second substance may be 4-mercaptophenylboronic acid.

With the above construction, surface-enhanced Raman-scattered light having sharp peaks can be generated. Also, signals with high intensity can be provided. Furthermore, the influences of obstructing components such as proteins in the biological body can be reduced.

An embodiment of the present disclosure can be used for detecting an analyte in a biological body or a subject solution (e.g., a biological component such as glucose), or measuring the concentration thereof.

While the present invention has been described with respect to exemplary embodiments thereof, it will be apparent to those skilled in the art that the disclosed invention may be modified in numerous ways and may assume many embodiments other than those specifically described above. Accordingly, it is intended by the appended claims to cover all modifications of the invention that fall within the true spirit and scope of the invention.

What is claimed is:

1. A method for detecting an analyte, comprising:
   providing a detection apparatus,
      the detection apparatus including a light source and a spectrometer;

irradiating a sensor chip with excitation light from the light source to generate first surface-enhanced Raman-scattered light having a first peak and second surface-enhanced Raman-scattered light having a second peak different from the first peak,
the sensor chip including:
a substrate,
a metal pattern formed on a side of the substrate that is irradiated with the excitation light, and
a first substance and a second substance different from the analyte to be detected and provided near the metal pattern, wherein,
the first substance generates the first surface-enhanced Raman-scattered light,
a first intensity Xa which is an intensity of the first surface-enhanced Raman-scattered light does not vary with changes in concentration of the analyte,
the second substance generates the second surface-enhanced Raman-scattered light, and
a second intensity Xb which is an intensity of the second surface-enhanced Raman-scattered light varies with changes in the concentration of the analyte;
detecting the first surface-enhanced Raman-scattered light from the first substance with the spectrometer to obtain the first intensity Xa;
simultaneously with detecting the first surface-enhanced Raman-scattered light, detecting the second surface-enhanced Raman-scattered light from the second substance with the spectrometer to obtain the second intensity Xb; and
calculating a value Xc resulting from dividing the second intensity Xb with the first intensity Xa having been measured simultaneously with the second intensity Xb.

2. The method of claim 1, wherein:
the detection apparatus includes a memory retaining information indicating correlation between the value Xc and the concentration of the analyte, and
the step of calculating the value Xc comprises calculating the concentration of the analyte based on the value Xc and the information.

3. The method of claim 2, wherein:
the sensor chip is embedded in a biological body, and
the concentration of the analyte contained in the biological body is calculated.

4. The method of claim 1, wherein the analyte is glucose.

5. The method of claim 4, wherein:
the first substance is monochloro-para-xylylene polymer, and
the second substance is 4-mercaptophenylboronic acid.

6. The method of claim 5, wherein:
the first peak of the first surface-enhanced Raman-scattered light is at 1209 $cm^{-1}$, and
the second peak of the second surface-enhanced Raman-scattered light is at 1076 $cm^{-1}$.

7. A detection system for detecting an analyte, comprising:
a detection apparatus; and
a sensor chip, wherein:

the detection apparatus includes a light source and a spectrometer,
the sensor chip includes:
a substrate;
a metal pattern formed on a side of the substrate that is irradiated with excitation light from the light source; and
a first substance and a second substance different from the analyte to be detected and provided near the metal pattern,
the first substance generates first surface-enhanced Raman-scattered light having a first peak,
a first intensity Xa which is an intensity of the first surface-enhanced Raman-scattered light does not vary with changes in concentration of the analyte,
the second substance generates second surface-enhanced Raman-scattered light having a second peak different from the first peak,
a second intensity Xb which is an intensity of the second surface-enhanced Raman-scattered light varies with changes in the concentration of the analyte, and
the detection system:
irradiates the sensor chip with the excitation light to generate the first surface-enhanced Raman-scattered light and the second surface-enhanced Raman-scattered light,
detects the first surface-enhanced Raman-scattered light from the first substance with the spectrometer to obtain the first intensity Xa, and simultaneously detects the second surface-enhanced Raman-scattered light from the second substance with the spectrometer to obtain the second intensity Xb, and
calculates a value Xc resulting from dividing the second intensity Xb with the first intensity Xa having been measured simultaneously with the second intensity Xb.

8. The detection system of claim 7, wherein:
the detection apparatus includes a memory retaining information indicating correlation between the value Xc and the concentration of the analyte, and
the detection system calculates the concentration of the analyte based on the value Xc and the information.

9. The detection system of claim 8, wherein: the sensor chip is configured to be embedded in a biological body, and the detection system calculates the concentration of the analyte contained in the biological body.

10. The detection system of claim 7, wherein the analyte is glucose.

11. The detection system of claim 10, wherein:
the first substance is monochloro-para-xylylene polymer, and
the second substance is 4-mercaptophenylboronic acid.

12. The detection system of claim 11, wherein:
the first peak of the first surface-enhanced Raman-scattered light is at 1209 $cm^{-1}$, and
the second peak of the second surface-enhanced Raman-scattered light is at 1076 $cm^{-1}$.

* * * * *